US007259843B2

(12) United States Patent
Naganuma et al.

(10) Patent No.: US 7,259,843 B2
(45) Date of Patent: Aug. 21, 2007

(54) FOREIGN MATTER DETECTION AND REMOVAL DEVICE

(75) Inventors: Tatsuo Naganuma, Kanagawa-Ken (JP); Atsuo Ida, Kyoto-Fu (JP); Takao Arai, Kyoto-Fu (JP); Shoji Noda, Kyoto-Fu (JP)

(73) Assignee: Kirin Beverage Corporation, Chiyoda-Ku (JP)

( * ) Notice: Subject to any disclaimer, the term of this patent is extended or adjusted under 35 U.S.C. 154(b) by 252 days.

(21) Appl. No.: 10/533,646

(22) PCT Filed: Nov. 5, 2003

(86) PCT No.: PCT/JP03/14114

§ 371 (c)(1),
(2), (4) Date: May 3, 2005

(87) PCT Pub. No.: WO2004/041453

PCT Pub. Date: May 21, 2004

(65) Prior Publication Data

US 2006/0008560 A1   Jan. 12, 2006

(30) Foreign Application Priority Data

Nov. 5, 2002   (JP) .............................. 2002-321324

(51) Int. Cl.
  *G01N 21/00*   (2006.01)
(52) U.S. Cl. .................... 356/237.1; 356/335
(58) Field of Classification Search ...................... None
  See application file for complete search history.

(56) References Cited

U.S. PATENT DOCUMENTS 6,081,324 A * 6/2000 Yagita et al. ............ 356/237.1

7,092,084 B2 * 8/2006 Payne ........................ 356/246

FOREIGN PATENT DOCUMENTS

| JP | 15151/1989 | 1/1989 |
|---|---|---|
| JP | 04-054441 | 2/1992 |
| JP | 09-304412 | 11/1997 |
| JP | 10-043695 | 2/1998 |
| JP | 10-300680 | 11/1998 |
| JP | 10-318931 | 12/1998 |

* cited by examiner

*Primary Examiner*—Michael P. Stafira
(74) *Attorney, Agent, or Firm*—Darby & Darby

(57) ABSTRACT

A foreign matter detecting and eliminating system detects and eliminates foreign matters included in a fluid, such as a fruit juice containing fibrous materials, a beverage and a liquid medicine. The foreign matter detecting and eliminating system includes: a tubular distribution head 6 having one closed end and one open end connected to a feed line for carrying a fluid and provided with a plurality of axially arranged oblong slits 11; a plurality of main passages 7 having a flat sectional shape and communicating with the interior of the distribution head 6 by means of the oblong slits 11; an optical foreign matter detecting device 14 combined with the main passages 7 to detect foreign matters included in the fluid flowing through the main passages 7; and foreign matter eliminating devices 15 disposed below the foreign matter detecting device 14 with respect to the flowing direction of the fluid and capable operating in response to a foreign matter detection signal provided by the foreign matter detecting device 14 to discharge a predetermined quantity of the fluid containing foreign matters.

6 Claims, 10 Drawing Sheets

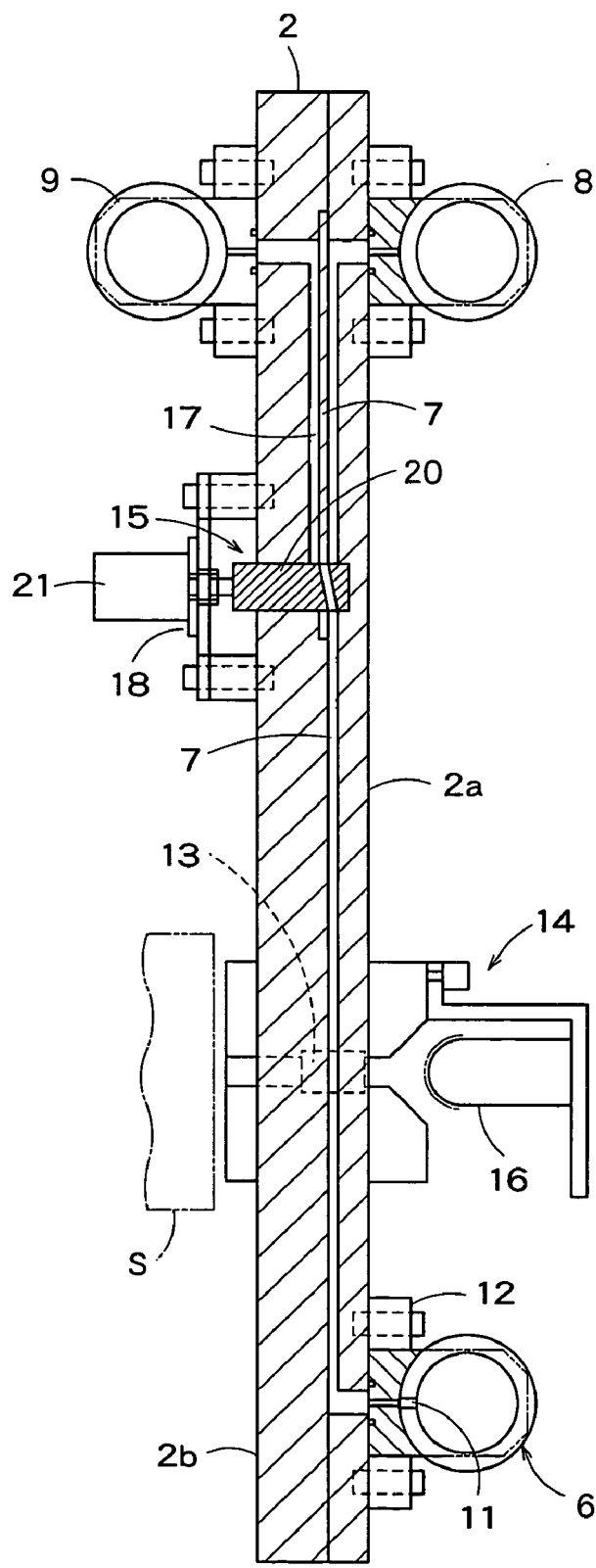
F I G. 6

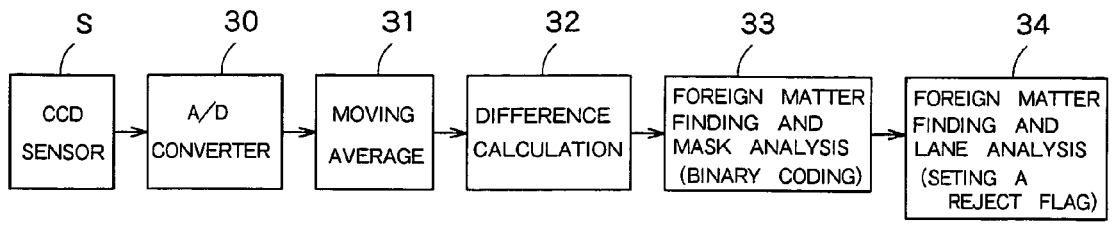
F I G. 9
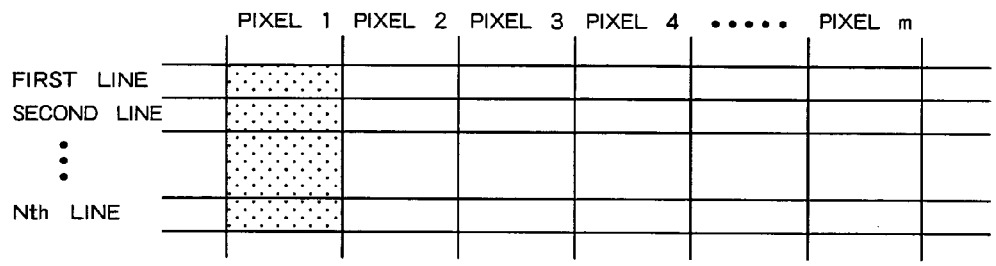
F I G. 10
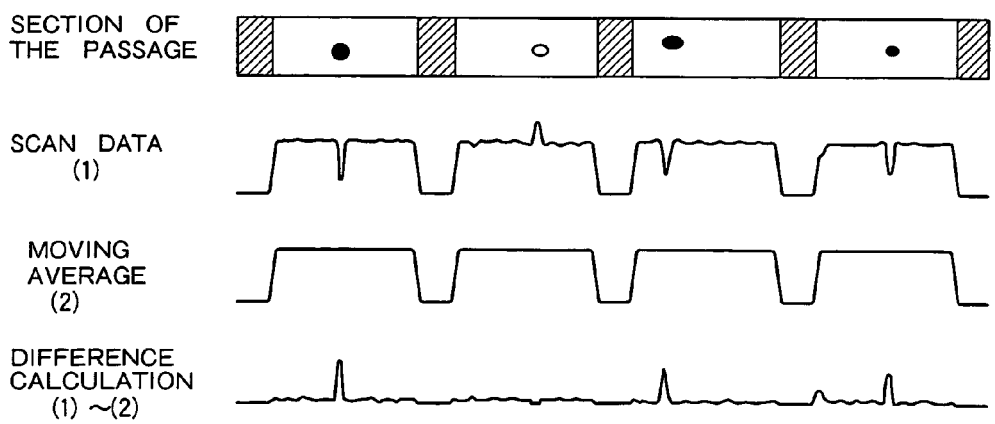
F I G. 11

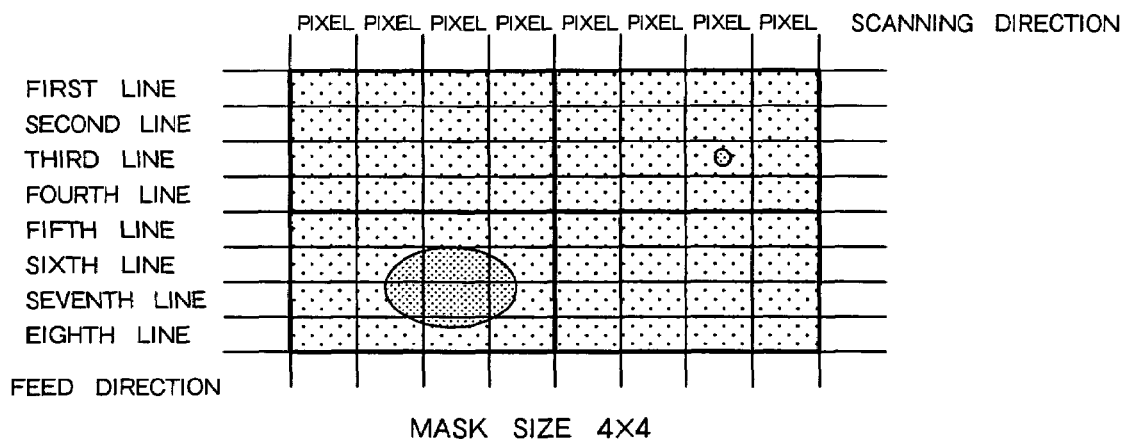
F I G. 12
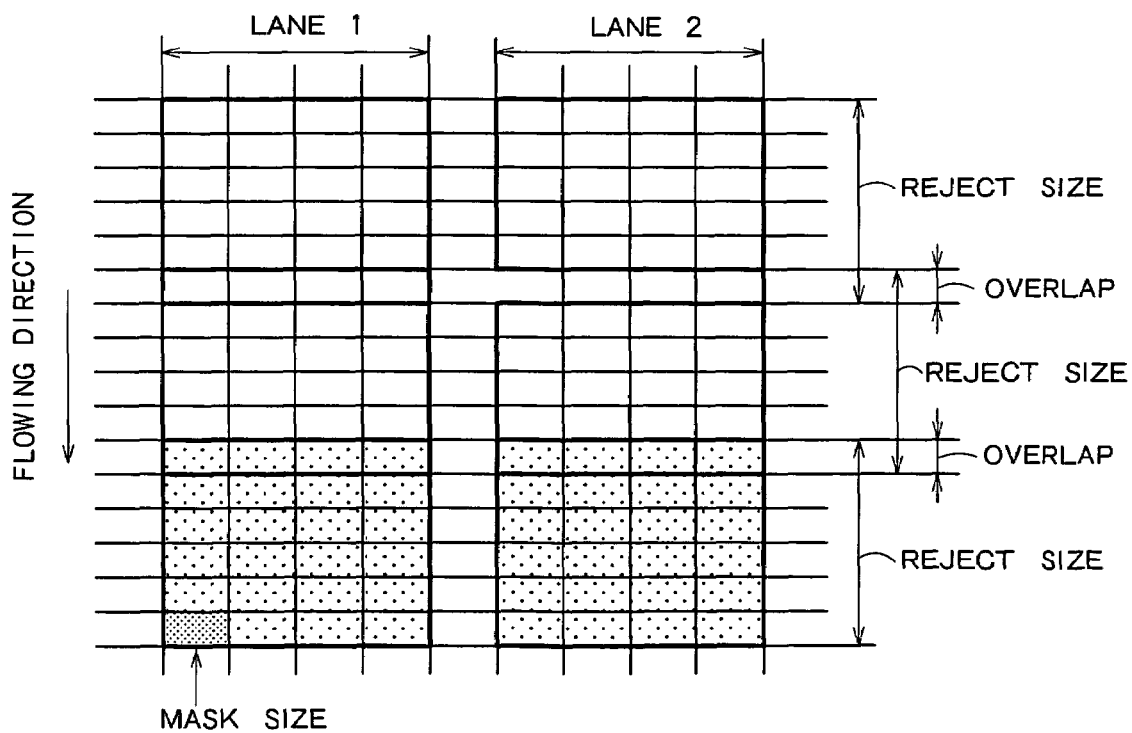
F I G. 13

FOREIGN MATTER DETECTION AND REMOVAL DEVICE

This is a U.S. national phase application under 35 U.S.C. § 371 of International Patent Application No. PCT/JP2003/014114, filed Nov. 5, 2003 which claims the benefit of Japanese Application No. 2002-321324, filed Nov. 5, 2002. The International Application was published in Japanese on May 21, 2004 as International Publication No. WO/2004/041453 under PCT Article 21(2). The contents of both applications are incorporated by reference herein in their entirety.

FIELD OF THE INVENTION

The present invention relates to a foreign matter detecting and eliminating system for detecting and eliminating foreign matters included in a flowing liquid, such as a fruit juice containing fibrous materials, a beverage and a liquid medicine.

BACKGROUND ART

Filters cannot be applied to filtering out foreign matters included in a fluid, such as a fruit juice containing fibrous materials because filters are clogged up with the fibrous materials.

A previously proposed apparatus for eliminating foreign matters included in such a fluid guides the fluid into a plurality of narrow passages by gravity, monitors the fluid flowing through the narrow passages by detectors, and opens a valve placed in the narrow passage upon the detection of a foreign matter included in the fluid flowing through the same narrow passage by the detector to discharge the foreign matter from the narrow passage (Patent document 1).

A previously proposed fibrous matter detecting and eliminating apparatus for detecting and eliminating foreign matters included in a fluid uses a fluid carrying pipe provided with an inspection window, illuminates the fluid through the inspection window by an illuminating means, measures transmitted light transmitted by the fluid or reflected light reflected by the fluid, converts the transmitted or reflected light into an image signal, compares a signal level based on the image signal with a reference signal level to decide where or not the fluid includes foreign matters, and eliminates the foreign matters when it is decided that the fluid includes foreign matters (Patent document 2)

Patent document 1: JP 10-43695 A

Patent document 2: JP 2000-235004 A

The apparatus mentioned in Patent document 1 uses the pressure head of the fluid to guide the fluid into the narrow passages by gravity. Therefore, the fluid is not distributed uniformly to the narrow passages in the middle part and those in the end parts of the apparatus, different pressures act on the narrow passages, and the velocity of the fluid in the narrow passage nearest to a supply line and that of the fluid in the narrow passage farthest from the supply line are liable to differ from each other. Consequently, foreign matters cannot be eliminated with reliability and the fluid cannot be processed at a high processing speed.

Since reflected light is used for detecting foreign matters, the detector has difficulty in detecting foreign matters in the middle layer of the flow of the fluid when the tint of foreign matters is similar to that of the fluid or when foreign matters are small as compared with the length of a detecting optical path. Thus the apparatus is unable to detect foreign matters in high detecting accuracy at a high processing speed.

The fibrous matter detecting and eliminating apparatus mentioned in Patent document 2 uses a pipe having a circular cross section and provided with an inspection window. Although this apparatus is applicable to detecting and eliminating foreign matters included in a fluid having a high transparency, the same is not applicable to detecting and eliminating foreign matters included in a fluid having a low transparency, such as a fruit juice containing fibrous materials, because the inspecting light is unable to penetrate the fluid diametrically.

As mentioned above, fluids, such as beverages including fibrous components and liquid medicines, clog up filters and the fibrous components included therein make the detection of foreign matters difficult.

Since the transparency of fruit juices is particularly low, optical detection of foreign matters included in fruit juices is difficult. Therefore, the optical detection of foreign matters needs to use an optical path of the shortest possible length and to use an algorithm that will not mistake fibrous components or bubbles often adhering to fibrous components for foreign matters.

The passage must be divided into narrow passages and make the fluid flow at the same velocity through all the narrow passages to eliminate foreign matters completely and to reduce the quantity of the fluid that is removed together with foreign matters.

It is important in detecting and eliminating foreign matters included in a fluid including such kind of fibrous components to distribute the fluid uniformly into narrow passages by pressure and to avoid clogging the narrow passage even if the fluid includes fibrous components.

DISCLOSURE OF THE INVENTION

According to the present invention, a fluid is made to flow through a distribution head provided with a plurality of axially arranged slits into a plurality of main passages having a flat sectional shape, the filtering effect of the slits of the distribution head is used to prevent the main passages from being clogged by preventing the flow of excessively large foreign matters into the main passages.

An optical foreign matter detecting means is placed in each of the main passages to detect foreign matters included in the fluid flowing through the main passage, and a foreign matter eliminating device that operates in response to a detection signal provided by the optical foreign matter detecting means is placed below the optical foreign matter detecting means in the main passage to eliminate foreign matters detected by the optical foreign matter detecting means.

Since the optical foreign matter detecting means detects foreign matters flowing through the main passage of a flat sectional shape, the optical foreign detecting means is able to detect foreign matters surely even if the fluid is a fruit juice including fibrous components.

The slits of the distribution head are flat slits of a width substantially equal to or less than the thickness of the main passages, and the width and length of the slits are dependent on a required fluid processing rate and a presumed size of foreign matters. The slits function as a filter that stops foreign matters of sizes greater than the width of the slits.

The foreign matter detecting means uses transmitted light for detecting foreign matters included in a fluid, such as a fruit juice including fibrous components or a liquid medicine, and detects foreign matters by sensing shades of the foreign matters intercepting the transmitted light.

When the foreign matters included in the fluid have an optically opaque part, information about the foreign matters can be processed at a high processing speed by using a monochromatic CCD sensor regardless of the color of the foreign matters and color difference between the fluid and the foreign matters. Even if the fluid includes much fibrous components or bubbles, only edges of semitransparent foreign matters are detected and the fibrous components or the bubbles can be regarded as noise and can be discriminated from foreign matters that need to be eliminated.

A foreign matter detecting and eliminating system according to the present invention is formed in a completely closed system to avoid causing secondary contamination by the foreign matter detecting and eliminating system when the foreign matter detecting and eliminating system is incorporated into a production line.

Foreign matter eliminating passages are formed parallel to the main passages below the foreign matter detecting means, the foreign matter eliminating passages are formed in a sectional area equal to that of the main passages, and the sum of the respective effective sectional areas of the main passage and the associated foreign matter eliminating passage is constant even in a state where a selector valve (reject valve) included in the foreign matter eliminating device is in operation. Thus, the flow velocity of the fluid is not affected by a foreign matter eliminating operation and is always constant, and the passage can be changed scarcely affecting the detecting operation of the foreign matter detecting device.

Desirably, the least possible quantity of the fluid is discharged when foreign matters are eliminated.

In a conventional completely sealed system, a fluid is divided and the divided fluid is discharged by operating a solenoid valve or a pneumatic valve. A know valve intended to handle a small quantity of a fluid is liable to be clogged with fibrous components and cannot be applied to handling this type of fluid.

The reject valve employed in the present invention for eliminating foreign matters has improved construction, the flow velocity of the fluid is determined from a flow rate measured by a flow meter or is calculated on the basis of the operating speed of a fluid supply pump, a working time proportional to the flow velocity for which the reject valve works is determined, and the fluid is discharged at a fixed discharge rate regardless of the variation of the fluid processing rate (flow velocity) in a range determined by taking electrical and physical delays in the operation of the reject valve into consideration to avoid discharging an excessively large quantity of the fluid even during a high-speed operation.

A foreign matter detecting and eliminating system according to the present invention includes: a tubular distribution head having one closed end and one open end connected to a feed line for carrying a fluid and provided with a plurality of axially arranged oblong slits; a plurality of main passages having a flat sectional shape and communicating with the interior of the distribution head by means of the oblong slits; an optical foreign matter detecting means combined with the main passages to detect foreign matters included in the fluid flowing through the main passages; and foreign matter eliminating devices disposed below the foreign matter detecting means with respect to the flowing direction of the fluid and capable operating in response to a foreign matter detection signal provided by the foreign matter detecting means to discharge a predetermined quantity of the fluid containing foreign matters.

Preferably, the width of the oblong slits of the distribution head is determined on the basis of a required fluid processing rate at which the fluid is to be processed and presumed sizes of foreign matters and is equal to or less than the thickness of a section of the main passages.

Preferably, the foreign matter detecting means includes: an illuminating means disposed so as to face inspection parts each formed by covering openings formed in side walls defining the main passage so as to open into the main passage with transparent members to emit light toward the inspection parts, and a CCD sensor for receiving light emitted by the light emitting means and transmitted by the fluid flowing through the main passages to detect foreign matters; wherein foreign matters are detected by comparing the moving average of an analog signal provided by the CCD sensor and a signal provided in each scanning cycle and calculating the difference between the moving average and the signal provided in each scanning cycle.

Preferably, foreign matter eliminating passages are formed parallel to the main passages below the foreign matter detecting means, the foreign matter eliminating passages are formed in a sectional area equal to that of the main passages, a reject valve is placed at an upper end, with respect to the flowing direction of the fluid, of each foreign matter eliminating passage to connect the main passage to and disconnecting the same from the foreign matter eliminating passage, and the sum of the respective effective sectional areas of the main passage and the associated foreign matter eliminating passage is constant even in a state where the reject valve is in a passage changing operation.

Preferably, each of the reject valves has a valve element slidably fitted in a cylindrical valve hole perpendicular to the main passage, and a driving unit for operating the valve element; and the valve element is provided with a skew through hole for connecting the main passage and the foreign matter eliminating passage when the reject valve is driven for a passage changing operation.

Preferably, the foreign matter detecting and eliminating system further includes a means for measuring flow Art at which the fluid flows into the distribution head and calculating flow velocity at which the fluid flows; wherein working time of the reject valve is controlled according to the flow velocity of the fluid.

BRIEF DESCRIPTION OF THE DRAWINGS

FIG. 6 is a sectional view taken on the line A-A in FIG. 5;

FIG. 9 is a block diagram showing the flow of image data provided by a foreign matter detector;

FIG. 10 is a diagram of assistance in explaining moving average;

FIG. 11 is a diagram of assistance in explaining difference calculation;

FIG. 12 is a diagram of assistance in explaining foreign matter finding and mask analysis; and FIG. 13 is a diagram of assistance in explaining a foreign matter finding lane analysis.

BEST MODE FOR CARRYING OUT THE INVENTION

A foreign matter detecting and eliminating system in a preferred embodiment according to the present invention will be described with reference to the accompanying drawings.

Figure 1:
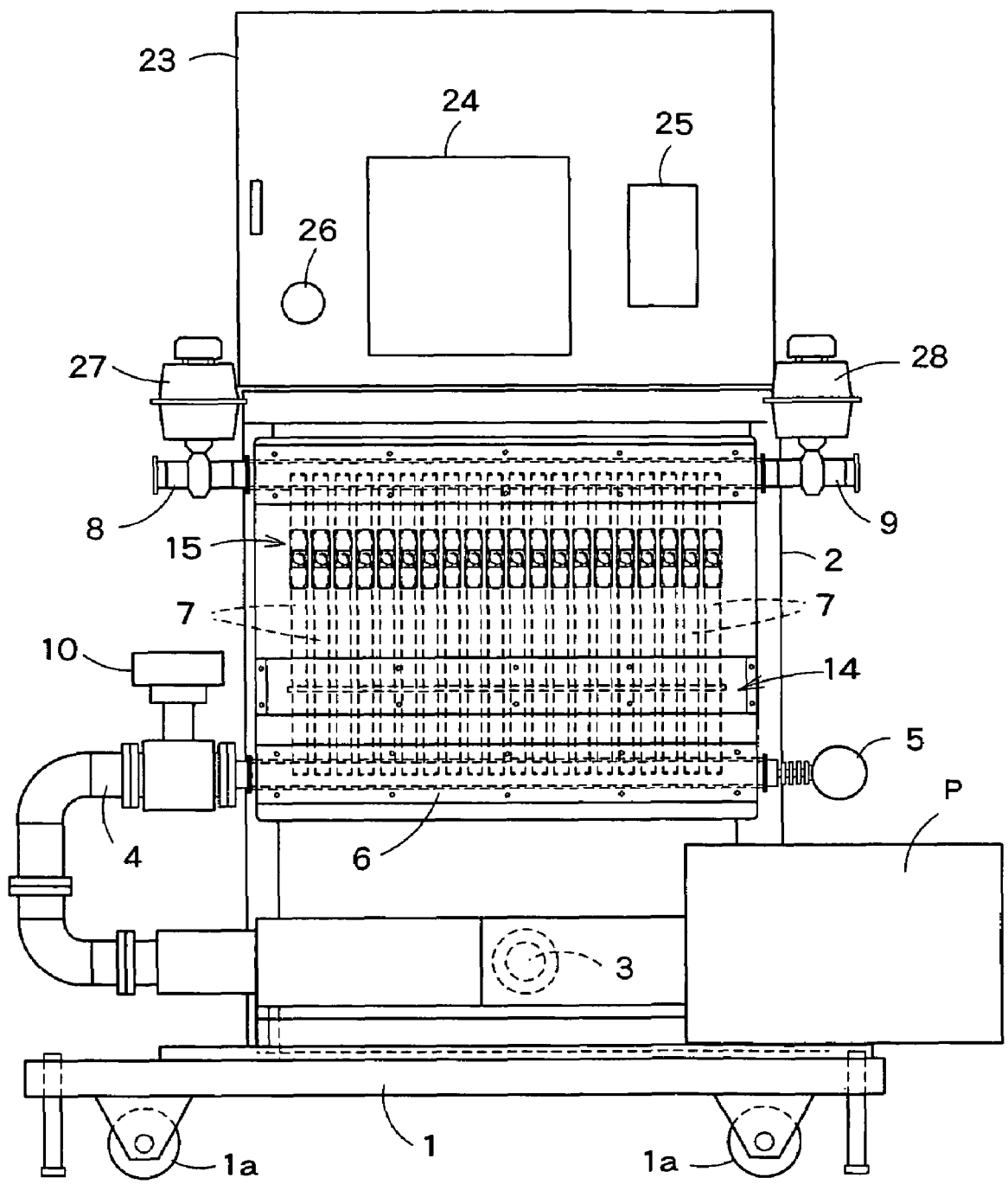
FIG. 1 is a front elevation of a foreign matter detecting and eliminating system in a preferred embodiment according to the present invention.
Figure 2:
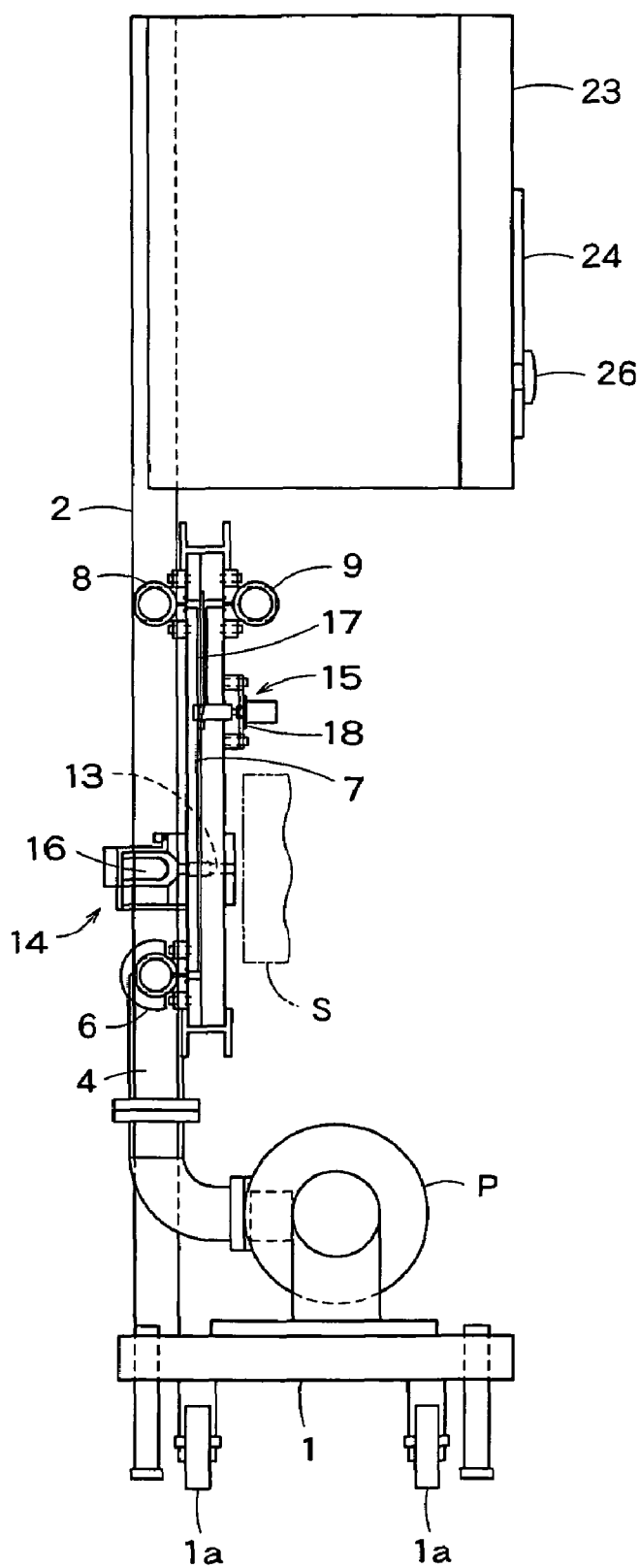
FIG. 2 is a side elevation of the foreign matter detecting and eliminating system shown in FIG. 1 taken from the left side of the foreign matter detecting and eliminating system.

FIG. 1 is a front elevation of the foreign matter detecting and eliminating system and FIG. 2 is a side elevation of the foreign matter detecting and eliminating system shown in FIG. 1 taken from the left side of the foreign matter detecting and eliminating system. In this embodiment, a fluid, such as a fruit juice, namely, a subject of inspection, is pumped so as to flow upward so that the weight of the fluid may not act. The foreign matter detecting and eliminating system is mounted on a movable carriage provided with wheels 1a.

A base 2 is set fixedly on the carriage 1 in a vertical position. The foreign matter detecting and eliminating system is held on the base 2.

The foreign matter detecting and eliminating system includes a pump P for pumping a fluid supplied from a tank, not shown, through a supply line 3, a distribution head 6 fixedly set in a horizontal position on a lower part of the base 2, having one open end connected to the pump P by a feed line 4 and the closed other end, a pressure gage 5 connected to the distribution head 6, a delivery pipe 8 and a reject pipe 9 through which foreign matters are recovered. The base is provided with a plurality of main passages 7, namely, twenty main passages 7 in this embodiment, each having one end connected to the distribution head 6 and the other end connected to the delivery pipe 8. Indicated at 10 is a flow meter for measuring the flow rate of the fluid in the feed line 4.

Figure 3:
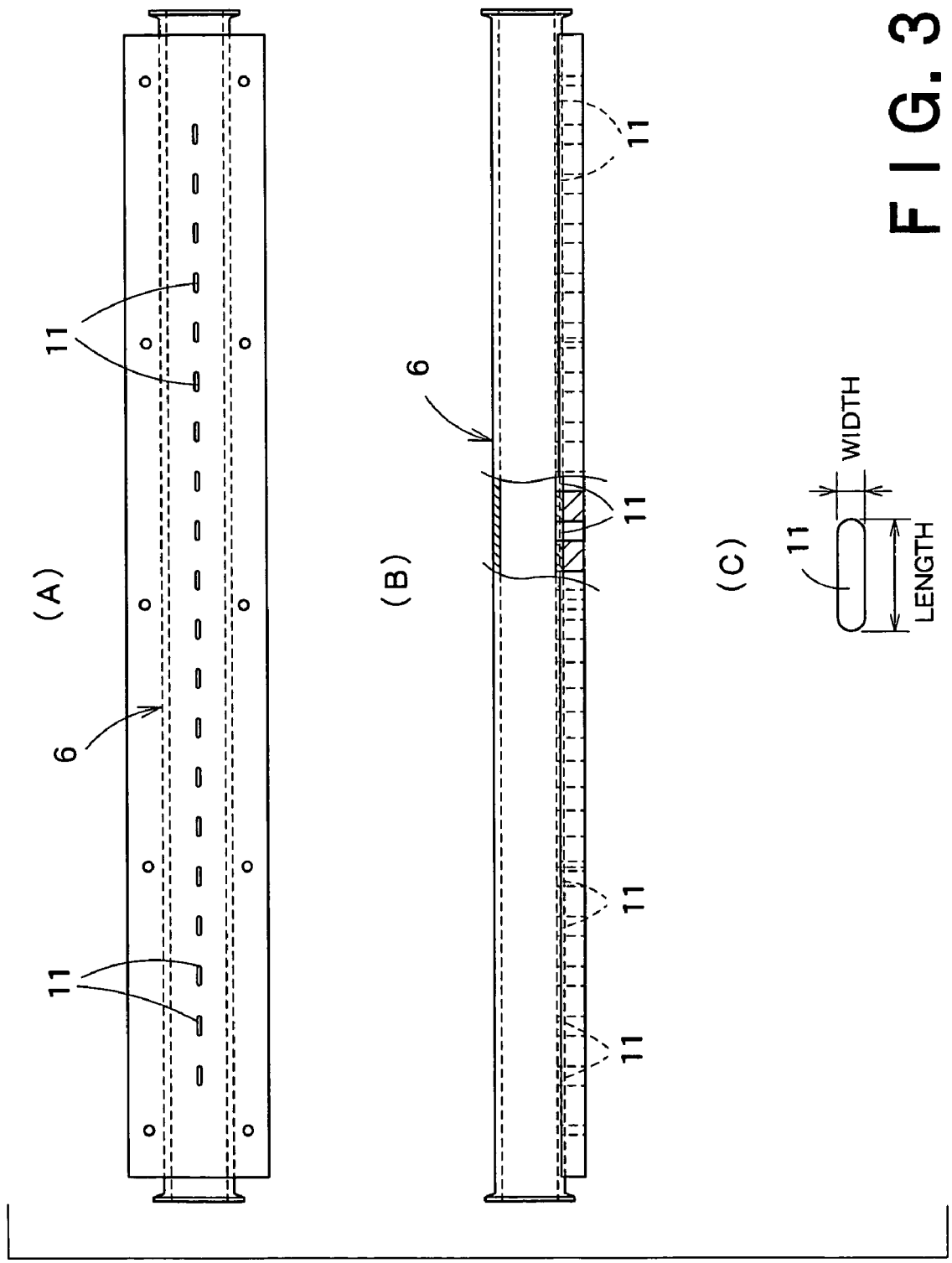
FIG. 3(A) is an enlarged front elevation of a distribution head shown in FIG. 1.
FIG. 3(B) is an enlarged plan view of the distribution head shown in FIG. 3(A)
FIG. 3(C) is an enlarged plan view of a slit.

As shown in FIGS. 3(A) and 3(B) in a front elevation and a plan view, the distribution head 6 is, for example, a stainless steel pipe having an inside diameter of 40 mm and provided with a plurality of slits 11 of an oblong shape, namely, twenty slits 11 of an oblong shape in this embodiment. The slits 11 are arranged along the axis of the distribution head 6.

Figure 4:
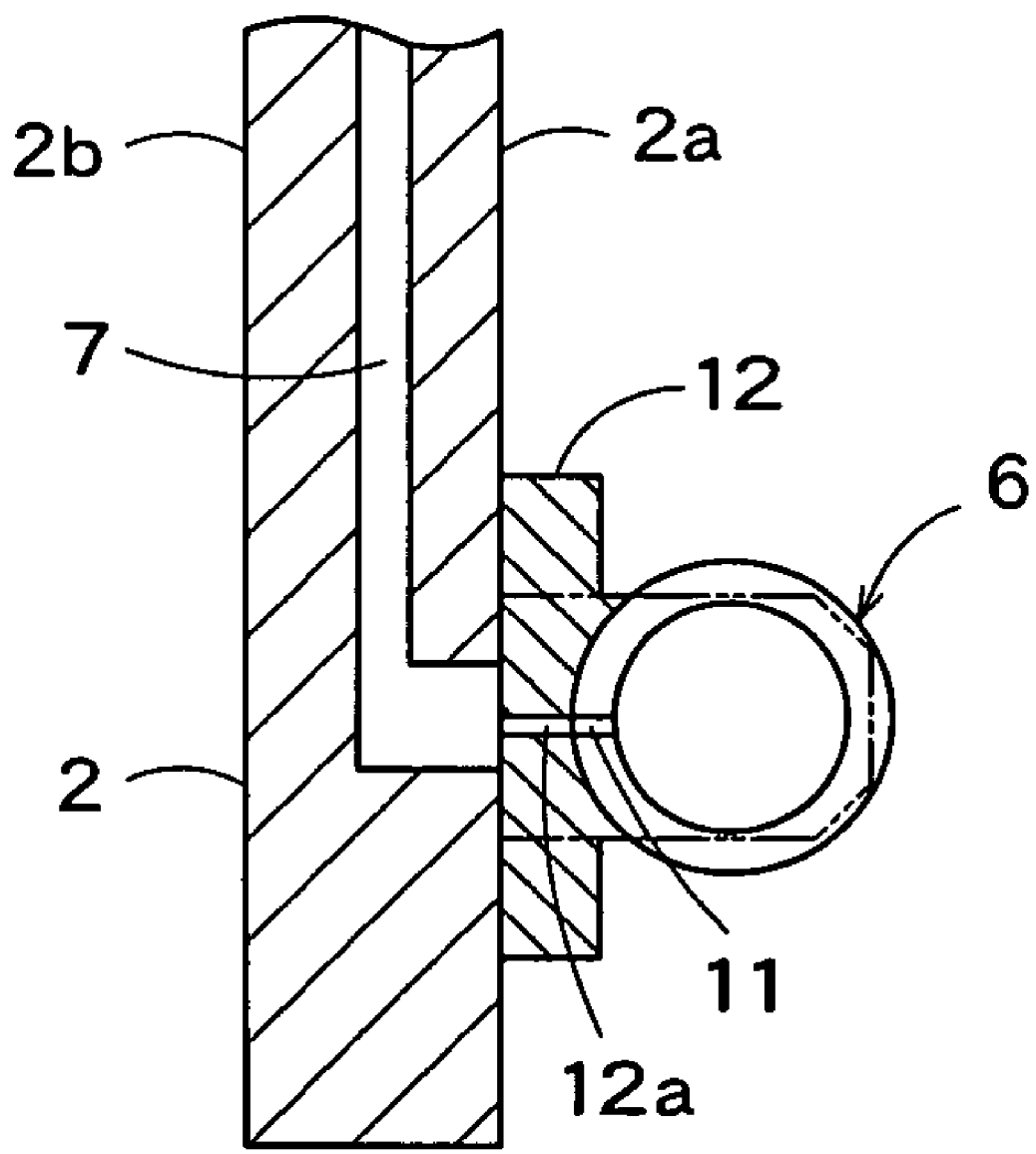
FIG. 4 is a fragmentary sectional view of the distribution head attached to a base.
Figure 5:
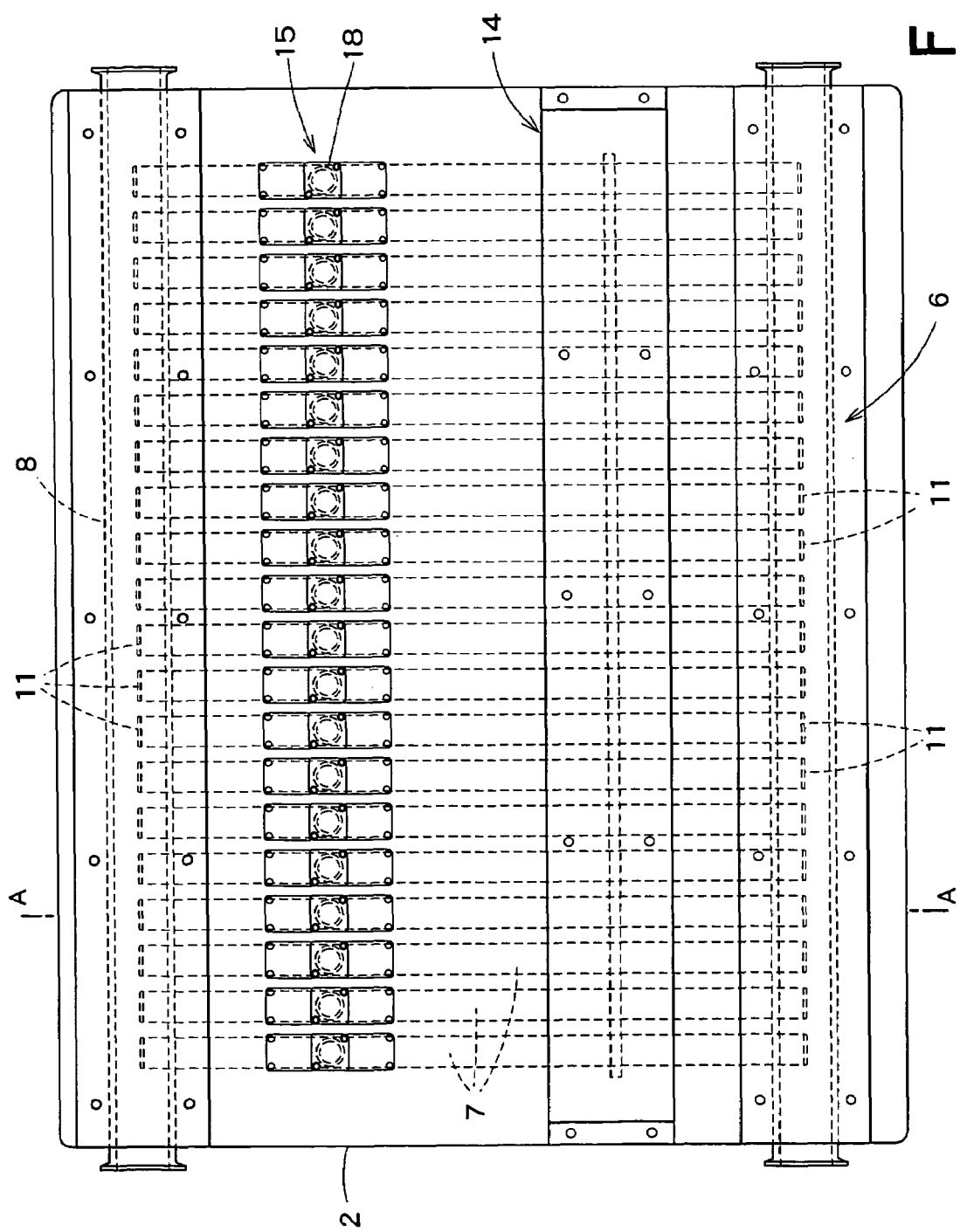
FIG. 5 is a front elevation of a main passage unit including the distribution head shown in FIG. 1.

The slits 11 are 6 mm in length and 2 mm in width. As shown in FIG. 4, the distribution head 6 is held fixedly on a lower part of the base 2 by a mounting fixture 12 such that the interior of the distribution head 6 communicates with the interiors of the main passages 7 by means of the slits 11 and through holes 12a formed in the mounting fixture 12.

The slits 11 have a filtering function. The slits 11 prevent foreign matter of sizes greater than their width from flowing from the distribution head 6 into the main passages 7 to prevent clogging the main passages 7 and loosen masses of fibrous components to disperse fibrous components.

The width of the slits 11 is properly determined according to the properties of the fluid and is not greater than the thickness of the section of the main passages 7. Although it is preferable that slits 11 are formed in an oblong shape having rounded opposite ends to facilitate machining, the slits 11 may be rectangular slits when the rectangular slits can be formed by machining.

As shown in FIGS. 2 and 6, the main passages 7 extend through inspection sections 13, respectively, a foreign matter detector 14 is disposed so as to correspond to the inspection sections 13, and foreign matter eliminating devices 15 are disposed below the foreign matter detector 14 with respect to the flowing direction of the fluid, i.e., above the foreign matter detector 14 in FIG. 6, so as to correspond to the main passages 7, respectively.

The inspection sections 13 are formed of a transparent material. As shown in FIG. 6, the foreign matter detector 14 disposed so as to correspond to the inspection section 13 has a light source 16, namely, illuminating means, and a CCD sensor (line sensor) S for receiving light emitted by the light source 16 and traveled through the fluid flowing through the inspection section 13. The foreign matter detector 14 scans the inspection sections 13 of all the main passages 7.

The main passages 7 have a flat sectional shape of, for example, 20 mm in width, 4 mm in thickness and about 420 mm in length. The base 2 is formed by sticking two plates 2a and 2b together. Grooves of dimensions equal to those of the main passages 7 are formed in the plate 2a, and the other plate 2b is bonded to the plate 2a to form the main passages 7.

Foreign matter eliminating passages 17 are formed parallel to lower parts, below the inspection sections 13 with respect to the flowing direction of the fluid, of the main passages 7, respectively. The foreign matter eliminating passages 17 have a flat sectional shape of the same sectional area as that of the main passages 7.

The lower ends, with respect to the flowing direction of the fluid, of the main passages 7 are connected to the delivery pipe 8. Lower ends of the foreign matter eliminating passages 17 are connected to the reject pipe 9.

Figure 7:
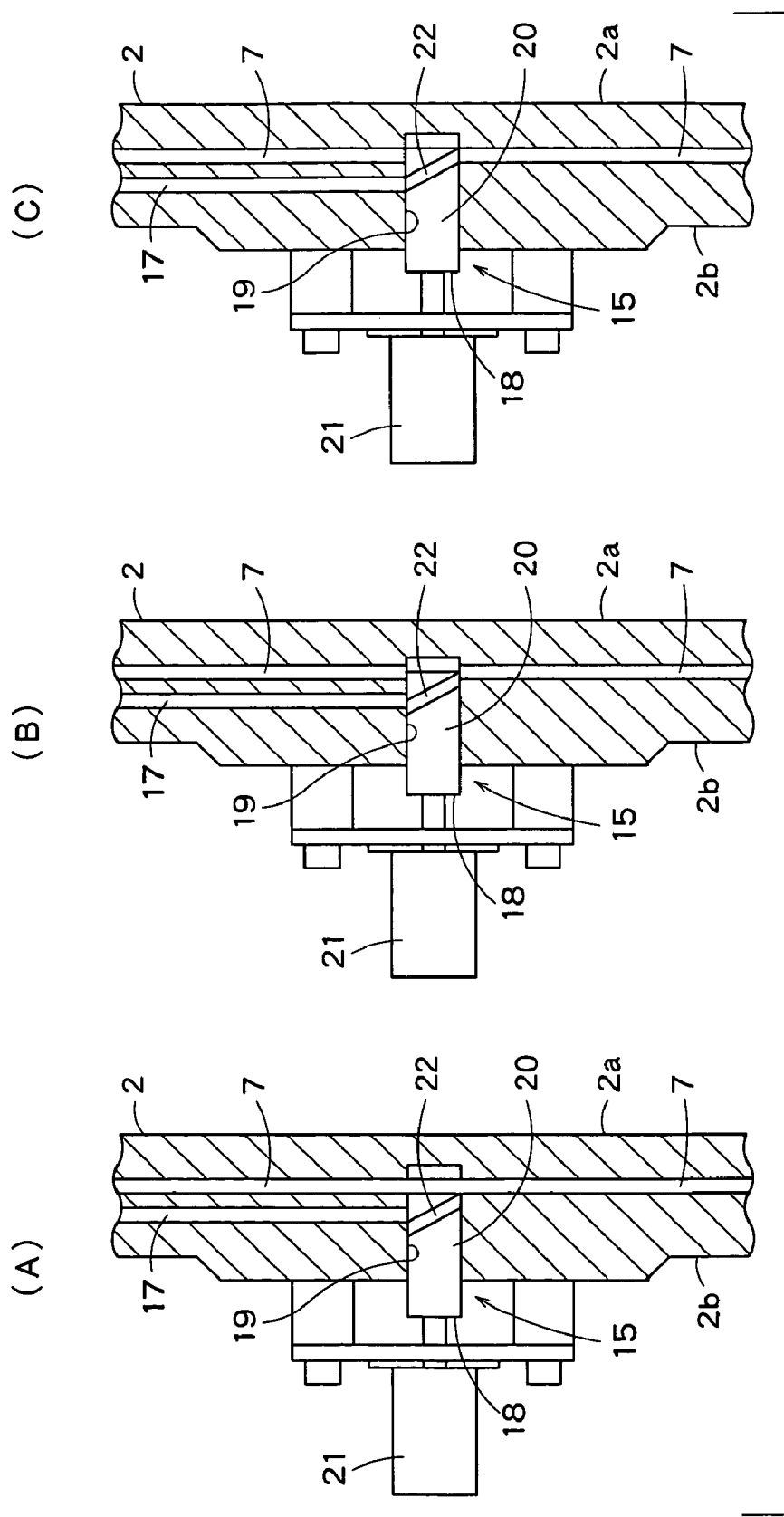
FIGS. 7(A), 7(B) and 7(C) are sectional view of a reject valve in a state where a valve element is at a position to open a main passage, in a state where the valve element is being turned to a foreign matter eliminating position and in a state where the valve element is set at the foreign matter eliminating position, respectively.

Foreign matter eliminating sections 15 correspond to the upper ends, with respect to the flowing direction of the fluid, of the foreign matter eliminating passages 17, respectively. Reject valves 18 are disposed so as to correspond to the foreign matter eliminating sections 15, respectively, as shown in FIGS. 6 and 7.

Each of the reject valves 18 has a cylindrical valve element 20 slidably fitted in a valve hole 19 formed in the base 2 perpendicularly to the main passage 7, and a driving device 21, such as a solenoid actuator or a pneumatic actuator, for axially moving the valve element 20 for a predetermined stroke.

Figure 8:
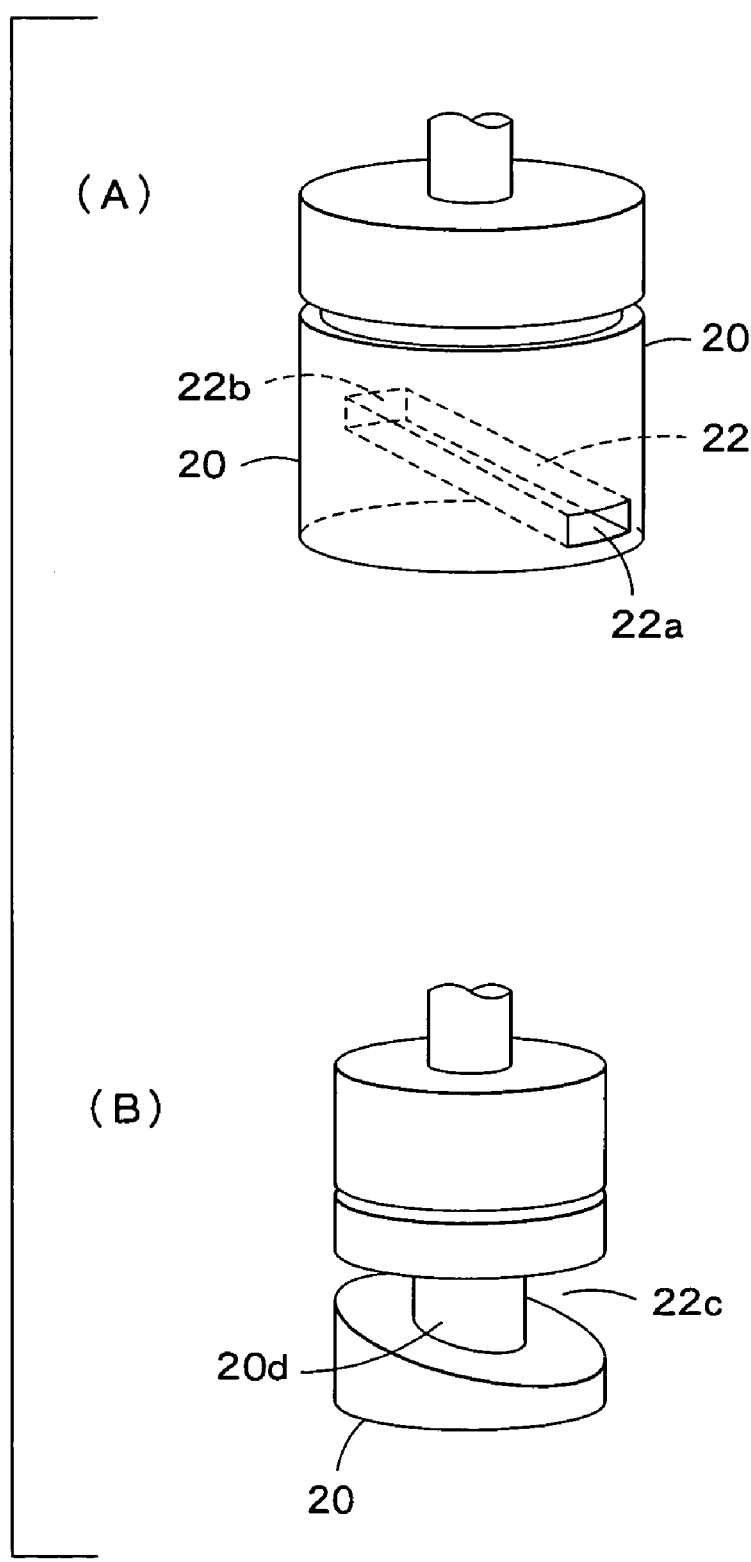
FIG. 8(A) is an enlarged perspective view of the valve element shown in FIG. 7.
FIG. 8(B) is an enlarged perspective view of a valve element in a modification.

As shown in FIG. 8(A), each valve element 20 is provided with a skew through hole 22 having an inlet 22a of a sectional shape corresponding to that of the end of a part, extending above the reject valve 18, of the main passage 7, and an outlet 22b of a sectional shape corresponding to that of the end of the foreign matter eliminating passage 17. The skew through hole 22 extends through the valve element 20 obliquely to the axis of the valve element 20.

The through hole 22 has a sectional area equal to those of the main passages 7 and the foreign matter eliminating passages 17. The through hole 22 is formed in a sectional area such that the sum of the respective effective sectional areas of the main passage 7 and the foreign matter eliminating passage 17 is constant even during the displacement of the valve element 20.

A valve element 20 in a modification shown in FIG. 8(B) is provided with a skew, annular groove 22c instead of the skew through hole 22. The skew, annular groove 22c extends around a core 20d.

Referring to FIG. 1, a control board 23 is attached to an upper part of the base 2, a control panel 24, a motor controller 25 and a safety button 26 are arranged on the control board 23. Automatic butterfly valves 27 and 28 are placed in the delivery pipe 8 and the reject pipe 9, respectively.

A foreign matter detecting method to be carried out by the foreign matter detector 14 will be described by way of example.

Relation Between Resolution and Processing Rate (Flow Rate)

The horizontal resolution of the CCD sensor S, namely, the resolution of the CCD sensor S with respect to the direction of flow of the fluid in the main passages 7, is dependent on the density of photocells. Then, the vertical resolution varies according to the flow velocity of the fluid. According to the principle, the scanning speed (charge storing time) is fixed and hence a distance traveled by the fluid during one scanning cycle is proportional to the flow velocity of the fluid. For example, the unit size of a CCD sensor of 300 dpi is 0.085 mm/pixel. Therefore, when the time of one scanning cycle is 0.418 ms and the flow velocity of the fluid is 195 mm/s, the fluid travels 0.082 mm in one scanning cycle, the horizontal and the vertical resolution are equal and a foreign matter of 0.3 mm included in the fluid is detected four times in one scanning cycle. Thus, foreign matters can be surely detected.

When the flow velocity of the fluid is 520 mm/s, about two and a half times 195 mm/s, the fluid travels 0.22 mm in one scanning cycle. Consequently, it is possible that a foreign matter of 0.3 mm cannot be detected. However, it is possible to detect foreign matter of sizes in the range of about 0.5 to about 1 mm without fail.

Detection Algorithm (FIG. 9)

(1) CCD Sensor S and a/D Converter 30

An A/D converter 30 converts an analog signal provided by the CCD sensor S into a corresponding 8-bit digital signal of 0 to 255 (0: Black, 255: White)

(2) Moving Average 31 (FIG. 10)

An average of pixel data on several lines read from the CCD sensor S is calculated. The moving average corresponds to the concentration of a stock solution. The moving average is updated every several lines. The number of lines may be changed.

(3) Difference Calculation 32 (FIG. 11)

The average calculated by the moving average 31 is subtracted from data read from the CCD sensor S to cancel out the concentration of the stock solution. Thus, a matter having a concentration different from that of the stock solution is extracted.

When (Scan data)<(Average), it is decided that the scan data includes data on the shade of a foreign matter or the like. When (Scan data)>(Average), it is decided that the fluid includes a bright matter, such as the skin or string of fruit. Thus, only dark foreign matters are detected by Difference calculation 32.

(4) Foreign Matter Finding and Mask Analysis (FIG. 12)

Data obtained by difference calculation and a foreign matter slice are compared to find a foreign matter. When comparison is made for each pixel, the comparison reacts sharply on noise corresponding to one pixel, such as a dust particle and noise is regarded as a foreign matter. To avoid such mistaken decision, a mask area including a plurality of pixels is defined and the average of data on the pixels in the mask area is used for finding foreign matters. The size of the mask area is optional. The data obtained by mask analysis is given to a step for foreign matter finding and lane analysis 34.

(5) Foreign Matter Finding and Lane Analysis 34 (FIG. 13)

When even a single foreign matter is included in a mask of one reject size area in each lane, a reject flag is set and the data is written to a memory.

The reject size is dependent on the working time, namely, an open time or a closed time, of the reject valve 18. The reject size is large and the amount of the discharged fluid increases when the working time is long. An overlap is determined taking into consideration a time necessary for the stroke of the valve element 20 of the reject valve 18.

(6) A reject flag in the 1 state or the 0 state is stored in a memory. After calculating a delay time based on the flow velocity and an operating time, the driving device 21 is controlled.

When the foreign matter detector 14 detects foreign mattes by this foreign matter detecting method, an operation for adjusting parameters mentioned in Patent document 1 is not necessary even if the type or lot of the fluid is changed or properties of the fluid of a batch change. Patent document 1 that amplifies a change by the product of optional measured data amplifies noise also. Therefore, small foreign matters as compared with the width of the passage (CCD sensor) cannot be detected. The foregoing foreign matter detecting method is able to detect such small foreign matters.

The operation of the foreign matter detecting and eliminating system embodying the present invention will be described.

A fluid, such as a stock of fruit juice including fibrous components, stored in a tank is pumped by the pump P to supply the fluid through the feed line 4 to the distribution head 6.

The fluid flows uniformly through the oblong slits 11 of the distribution header 6 into the main passages 7. Large foreign matters unable to pass the oblong slits 11 are separated from the fluid and masses of fibrous components are loosened by the agency of the edges of the oblong slits 11 before the masses of fibrous components flow into the main passages 7. Thus the fluid is distributed uniformly to the main passages 7.

The foreign matter detector 14 inspects the fluid flowing through the main passages 7 to detect foreign matters. When a foreign matter is detected in the fluid flowing through the main passage 7, the reject valve 18 corresponding to the main passage 7 is changed from the state shown in FIG. 7(A) through the state shown in FIG. 7(B) into the state shown in FIG. 7(C) to connect the main passage 7 to the foreign matter eliminating passage 17 by the through hole 22 of the valve element 22.

The fluid including the foreign matter flows from the main passage 7 into the foreign matter eliminating passage 17 and is discharged outside through the reject pipe 9.

After a predetermined quantity of the fluid has flowed into the foreign matter eliminating passage 17, the reject valve 18 is set in the state shown in FIG. 7(A) to connect the upper part of the main passage 7 on the upper side of the reject valve 18 and the lower part of the same on the lower side of the reject valve 18 by the through hole 22 of the valve element 20 and to disconnect the foreign matter eliminating passage 17 from the main passage 7.

Although the position of the through hole 22 of the valve element 20 changes gradually during the operation of the reject valve 18 to change the valve element 20 from the position shown in FIG. 7(A) to the position shown in FIG. 7(C) and during the operation of the reject valve 18 to change the valve element 20 from the position shown in FIG. 7(C) to the position shown in FIG. 7(A), the sum of the respective effective sectional areas of the main passage 7 and the associated foreign matter eliminating passage 17 is constant. Therefore, the flow rate (flow velocity) of the fluid flowing through the main passage 7 does not vary even when part of the fluid flowing through the main passage 7 is directed into the foreign matter eliminating passage 17. Even if fibrous components of the fluid remain in a space between the valve element 20 and the main passage 7 during the movement of the valve element 20 to its home position shown in FIG. 7(A), the remaining fibrous components are sheared by the edge of the valve element 20. Consequently, the movement of the valve element 20 is not obstructed by the fibrous components and the main passage 7 will not be clogged with the fibrous components.

The foreign matter detecting and eliminating system of the present invention of completely closed construction incorporated into the fluid supply line is able to eliminate foreign matters included in the fluid, namely, a product.

As apparent from the foregoing description, the foreign matter detecting and eliminating system of the present invention distributes a fluid, such as a fruit juice including fibrous components or a liquid medicine, supplied into the distribution head 6 through the oblong slits into the main passages. Therefore, large foreign matters of sizes greater than the width of the oblong slits are unable to flow into the main passages and hence the main passages and the foreign matter eliminating passages will not be clogged with such large foreign matters. Even if the fluid contains masses of fibrous components, the edges of the oblong slits loosen the masses of fibrous components and disperse the fibrous components and hence the main passages will not be clogged with masses of fibrous components.

When foreign matters included in the fluid have opaque parts, the foreign matters can be detected by the monochromatic CCD line sensor regardless of the colors of the foreign matters and the difference in color between the foreign matters and the fluid, and the fluid can be processed at a high processing rate.

Since negative signals are provided upon the detection of semitransparent things, fibrous components and bubbles included in the fluid, are regarded as noise, the fibrous components and bubbles are not eliminated.

Since the foreign matter detecting and eliminating system is a closed system, the foreign matter detecting and eliminating system incorporated into a production line will not contaminate the production line. Since the sum of the respective effective sectional areas of the main passage and the associated foreign matter eliminating passage is constant even in a state where the reject valve included in the foreign matter eliminating device is in operation, the passage can be changed without causing the flow velocity of the fluid to vary and foreign matters can be eliminated without trouble.

Since the quantity of the fluid discharged together with foreign matters can be reduced to the least possible extent and fibrous components remaining in a space between the valve element and the main passage are sheared by the sliding valve element when the reject valve operates, the movement of the valve element will not be obstructed by fibrous component and the reject valve will not malfunction.

A fixed quantity of the fluid can be discharged in a range determined by taking electrical and physical delays in the operation of the reject valve into consideration regardless of the processing rate (flow velocity) and hence it is possible to suppress increase in the quantity of the discharged fluid when the production line operates at a high processing rate.

The invention claimed is:

1. A foreign matter detecting and eliminating system comprising:
    a tubular distribution head having one closed end and one open end connected to a feed line for carrying a fluid and provided with a plurality of axially arranged oblong slits;
    a plurality of main passages having a flat sectional shape and communicating with the interior of the distribution head by means of the oblong slits;
    an optical foreign matter detecting means combined with the main passages to detect foreign matters included in the fluid flowing through the main passages; and
    foreign matter eliminating devices disposed below the foreign matter detecting means with respect to the flowing direction of the fluid and capable operating in response to a foreign matter detection signal provided by the foreign matter detecting means to discharge a predetermined quantity of the fluid containing foreign matters.

2. The foreign matter detecting and eliminating system according to claim 1, wherein the width of the oblong slits of the distribution head is determined on the basis of a required fluid processing rate at which the fluid is to be processed and presumed sizes of foreign matters and is equal to or less than the thickness of a section of the main passages.

3. The foreign matter detecting and eliminating system according to claim 1, wherein the foreign matter detecting means include:
    an illuminating means disposed so as to face inspection parts each formed by covering openings formed in side walls defining the main passage so as to open into the main passage with transparent members to emit light toward the inspection parts, and
    a CCD sensor for receiving light emitted by the light emitting means and transmitted by the fluid flowing through the main passages to detect foreign matters;
    wherein foreign matters are detected by comparing the moving average of an analog signal provided by the CCD sensor and a signal provided in each scanning cycle and calculating the difference between the moving average and the signal provided in each scanning cycle.

4. The foreign matter detecting and eliminating system according to claim 1, wherein foreign matter eliminating passages are formed parallel to the main passages below the foreign matter detecting means, the foreign matter eliminating passages are formed in a sectional area equal to that of the main passages, a reject valve is placed at an upper end, with respect to the flowing direction of the fluid, of each foreign matter eliminating passage to connect the main passage to and disconnecting the same from the foreign matter eliminating passage, and the sum of the respective effective sectional areas of the main passage and the associated foreign matter eliminating passage is constant even in a state where the reject valve is in a passage changing operation.

5. The foreign matter detecting and eliminating system according to claim 4, wherein each of the reject valves has a valve element slidably fitted in a cylindrical valve hole perpendicular to the main passage, and a driving unit for operating the valve element; and the valve element is provided with a skew through hole for connecting the main passage and the foreign matter eliminating passage when the reject valve is driven for a passage changing operation.

6. The foreign matter detecting and eliminating system according to claim 4 further comprising a means for measuring flow Art at which the fluid flows into the distribution head and calculating flow velocity at which the fluid flows; wherein working time of the reject valve is controlled according to the flow velocity of the fluid.

* * * * *